(12) United States Patent
Hanada et al.

(10) Patent No.: US 8,387,447 B2
(45) Date of Patent: Mar. 5, 2013

(54) PARTICULATE MATTER MEASURING DEVICE

(75) Inventors: Kazuo Hanada, Kyoto (JP); Yoshinori Otsuki, Kyoto (JP); Masayoshi Shinohara, Kyoto (JP)

(73) Assignee: Horiba, Ltd., Kyoto (JP)

( * ) Notice: Subject to any disclaimer, the term of this patent is extended or adjusted under 35 U.S.C. 154(b) by 274 days.

(21) Appl. No.: 13/018,561

(22) Filed: Feb. 1, 2011

(65) Prior Publication Data

US 2011/0192145 A1   Aug. 11, 2011

(30) Foreign Application Priority Data

Feb. 5, 2010   (JP) .................................. 2010-024163

(51) Int. Cl.
 *G01M 15/10*   (2006.01)
(52) U.S. Cl. .................................................. 73/114.71
(58) Field of Classification Search ............... 73/114.69, 73/114.71, 114.72, 114.73, 114.75
See application file for complete search history.

(56) References Cited

U.S. PATENT DOCUMENTS

| 8,141,413 | B2* | 3/2012 | Konstandopoulos et al. | 73/114.71 |
| 2004/0226354 | A1* | 11/2004 | Schmidt | 73/118.1 |
| 2006/0243026 | A1* | 11/2006 | Graze et al. | 73/23.31 |
| 2009/0287424 | A1* | 11/2009 | Nakamura | 702/24 |
| 2009/0320452 | A1* | 12/2009 | Gioannini et al. | 60/277 |
| 2010/0242457 | A1* | 9/2010 | Konstandopoulos et al. | 60/311 |
| 2011/0048105 | A1* | 3/2011 | Graze, Jr. | 73/23.31 |

FOREIGN PATENT DOCUMENTS

JP   2008-164413   7/2008

* cited by examiner

*Primary Examiner* — Eric S McCall
(74) *Attorney, Agent, or Firm* — Brooks Kushman P.C.

(57) ABSTRACT

An object of this invention is to improve resistance to heat and to increase a measurable range of a pressure without increasing a cost. In order to attain the object, a first unit arranged near an exhaust gas pipe and a second unit arranged separately from the first unit and connected to the first unit through a connecting pipe are provided, and the first unit has an exhaust gas flow channel from one end of which an exhaust gas is introduced, an orifice part arranged in a midst of the exhaust gas flow channel, a pressure rising check valve of a mechanically operating type that is connected to a downstream side of the orifice part in the exhaust gas flow channel, and a dilution gas flow channel that is connected to a downstream side of the orifice part in the exhaust gas flow channel so that the diluted exhaust gas diluted by the dilution gas is derived from the other end of the exhaust gas flow channel.

3 Claims, 4 Drawing Sheets

PARTICULATE MATTER MEASURING DEVICE

CROSS-REFERENCE TO RELATED APPLICATIONS

This application claims the benefit of JP 2010-024163 filed Feb. 5, 2010. The disclosure of which is incorporated in its entirety by reference herein.

FIELD OF THE ART

This invention relates to a particulate matter measurement device that measures particulate matters contained in an exhaust gas of an engine.

BACKGROUND ART

As a device that can accurately measure a number of particulate matters (PN: Particulate Number) contained in an exhaust gas, there is a particulate number counter called as, for example, a CPC (Condensation Particle Counter).

The CPC is to grow the particulate matters until a diameter of the particulate matter becomes big by passing the particulate matters in a supersaturated alcohol (butanol or the like) atmosphere followed by discharging the grown particulate matters from a slit and to count the discharged particulate matters by means of a laser light. Conventionally, as shown in the patent document 1, there is an integrated measurement unit comprising a single casing in which the CPC, a dilution mechanism to dilute the exhaust gas and a suction pump are housed. Then the measurement unit is arranged separately from an exhaust gas pipe and the measurement unit and the exhaust gas pipe are connected by a hot hose or the like and a rare exhaust gas from the exhaust gas pipe is diluted by means of the dilution mechanism housed in the measurement unit and introduced into the CPC. As mentioned, a reason why the hot hose is used as a piping is that a particulate matter is lost because the particulate matter attaches to the piping or the piping is clogged with the particulate matters attached to the piping if a temperature of the exhaust gas drops too much prior to dilution.

Prior Art Document

Patent Document

Patent document 1: Japan Patent laid-open number 2008-164413

DISCLOSURE OF THE INVENTION

Problems to be Solved by the Invention

Not all of the hot hoses have sufficient resistance to heat although the hot hose generates heat by itself In case that the hot hose is made of, for example, a resin material, the hot hose is generally inferior in heat resistance to an ordinary metal pipe. There is a case that a usage of the measurement unit is limited due to this property of the hot hose, or there is no other choice but to use an expensive hot hose having high resistance to heat.

In addition, a withstand pressure is determined for the measurement unit. The withstand pressure is an upper limit of the pressure allowed for the exhaust gas flowing into the measurement unit, and it is ordinarily determined by a capacity of a flow rate limit mechanism such as an orifice arranged at an inlet of the measurement unit. In order to raise the withstand pressure, simply, for example, an diameter of the orifice is made smaller. However, with this arrangement, in case that the pressure of the exhaust gas is low, namely, in case that the pressure of the exhaust gas is nearly equal to the atmospheric pressure, the pressure in the measurement unit becomes negative because of an action of the suction pump. As a result, it becomes difficult to control the flow rate of the exhaust gas introduced into the measurement unit and consequently there might be a fluctuation in the measurement accuracy.

Because of these reasons, conventionally, it is impossible to enlarge a measurable range of the pressure. Then in case that there is a request that the exhaust gas be sampled both at an upstream side and a downstream side of a diesel particulate filter in the exhaust gas pipe, it becomes difficult to measure a number of the particulate matters by the use of a common device if there is a big difference in the pressure between each point where the particulate matters are sampled due to a driving condition or a model of an engine.

The present claimed invention intends to solve all of the problems and a main object of this invention is to improve resistance to heat of the particulate matter measurement device and to increase the measurable range of the pressure of the exhaust gas without increasing the cost.

Means to Solve the Problems

Specifically, the particulate matter measurement device in accordance with this invention is to measure a particulate matter contained in an exhaust gas emitted from an internal combustion engine and comprises a first unit arranged near an exhaust gas pipe of the internal combustion engine, a second unit arranged separately from the first unit and a connecting pipe arranged between the first unit and the second unit.

And the particulate matter measurement device is characterized by that the first unit comprises a body that has an exhaust gas flow channel from one end of which the exhaust gas is introduced, an orifice part arranged in a midst of the exhaust gas flow channel, a pressure rising check valve that is connected to the exhaust gas flow channel and that prevents a rise of the pressure by letting a part of the exhaust gas escape with mechanically opened by the pressure at a time when the pressure in the exhaust gas flow channel becomes bigger than or equal to a certain amount, and a dilution gas flow channel that is connected to a downstream side of the orifice part in the exhaust gas flow channel and that introduces the dilution gas into the exhaust gas flow channel, wherein the body is so arranged to derive the diluted exhaust gas as being the exhaust gas diluted by the dilution gas from the other end of the exhaust gas flow channel, and the second unit comprises a particulate matter measurement mechanism that introduces the diluted exhaust gas derived from the first unit through the connecting pipe and that measures the particulate matter contained in the introduced diluted exhaust gas.

In accordance with this arrangement, since the particulate matter measurement device is divided into the first unit and the second unit and the first unit is arranged near the exhaust gas pipe, it is possible to make a length of the pipe from the exhaust gas pipe to the first unit extremely short. As a result, the temperature in the pipe will hardly drop at all so that it is possible to use a simple metal pipe as the pipe, thereby reducing the cost and also improving the resistance to heat.

In addition, since the heat of the exhaust gas pipe is transferred to the body of the first unit through the pipe, a heater with a small capacity at low cost will do as a heater arranged for the body. Contrary, it can be conceived that the body becomes at a high temperature due to the heat from the exhaust gas pipe, however, since only a simple mechanical component such as the orifice part or the pressure rising check valve is arranged for the body, it is possible to raise the resistance to heat without increasing the cost.

Furthermore, generally at a time when the temperature drops, the particulate matters attach to the pipe. However, since this invention has an arrangement that the exhaust gas is diluted at the same time when the temperature drops by introducing the dilution gas into the first unit, it is possible to prevent the particulate matters from attaching to the pipe as much as possible. Then there is no need of keeping the pipe at the downstream side of the first unit, namely, the connecting pipe between the first unit and the second unit at a high temperature. As a result, this arrangement also contributes to cost reduction and to simplification of the device.

In addition, since the orifice parts and the pressure rising check valves are arranged for the first unit, even though a case that the pressure in the exhaust gas pipe is approximate to the atmospheric pressure by the setting of the orifice valves, it is possible not to make the pressure in the first unit at a negative pressure. Furthermore, even though the pressure in the exhaust gas pipe becomes high by the setting of the orifice valves, it is possible to increase the resistance to pressure by keeping the pressure in the first unit at a pressure smaller than or equal to the set value, thereby expanding a measurable range of the pressure. As a result, this device can be applied not only to a usage wherein the pressure of the exhaust gas becomes considerably high such as a large-scaled engine or at the upstream side of the diesel particulate filter of the exhaust gas pipe but also to a usage wherein the pressure of the exhaust gas becomes considerably approximate to the atmospheric pressure. In addition, in case that the pressure fluctuation in the exhaust gas pipe is big, it is possible to secure the measurement accuracy.

In order to enlarge the measurable range of the pressure of the exhaust gas by improving the pressure resistance, it is preferable that a second orifice part is arranged on the upstream side of the orifice part in the exhaust gas flow channel, and a second pressure rising check valve is arranged between the orifice part and the second orifice part.

In order to connect the first unit and the exhaust gas pipe thermally securely and to make the first unit approach more to the exhaust gas pipe, it is preferable that the first unit further comprises a bracket mechanism for mounting the body on the exhaust gas pipe.

Effect of the Invention

In accordance with the above-mentioned presently claimed invention, since the particulate matter measurement device is divided into the first unit and the second unit and the first unit is arranged near the exhaust gas pipe and the exhaust gas is diluted by the first unit, it is possible to improve resistance to heat and also to reduce a cost.

In addition, since the orifice part and the mechanically operated pressure rising check valve are arranged for the first unit, it is possible to improve the resistance to pressure. Even though the pressure is low and near the atmospheric pressure, since it is possible not to make the pressure at a side of the particulate matter measurement device negative, the measurable range of the pressure can be enlarged.

BEST MODES OF EMBODYING THE INVENTION

One embodiment of this invention will be explained with reference to drawings.

Figure 1:
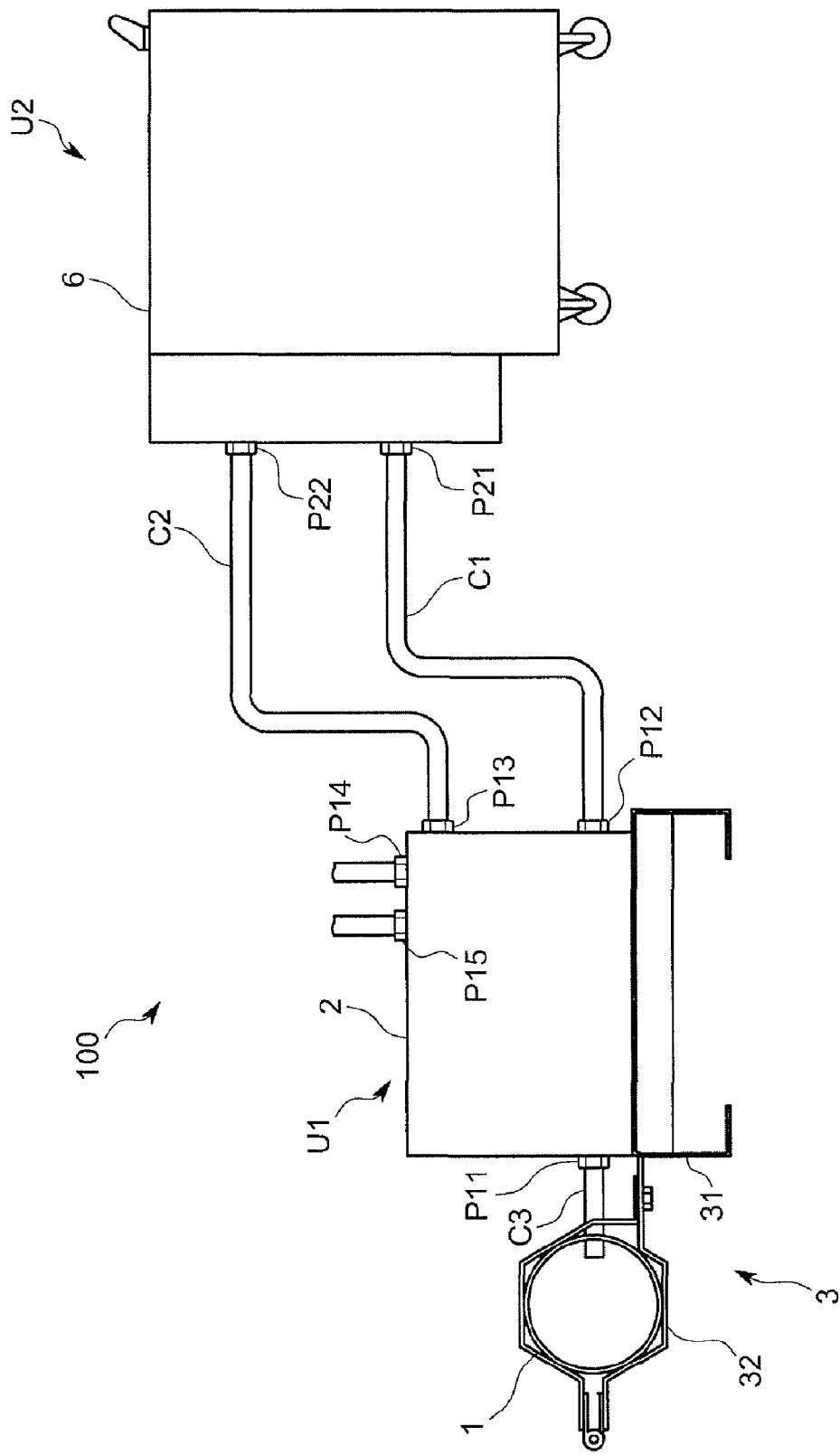
FIG. 1 is a pattern diagram showing an overall of a particulate matter measurement device in accordance with one embodiment of this invention.

A particulate matter measurement device 100 in accordance with this embodiment comprises, as its overall view is shown in FIG. 1, a first unit (U1) directly mounted on an exhaust gas pipe 1 of an internal combustion engine and a second unit (U2) arranged separately from the internal combustion engine.

The first unit (U1) comprises a body 2 arranged directly just beside of the exhaust gas pipe 1 and a bracket mechanism 3 for mounting the body 2 on the exhaust gas pipe 1.

Figure 3:
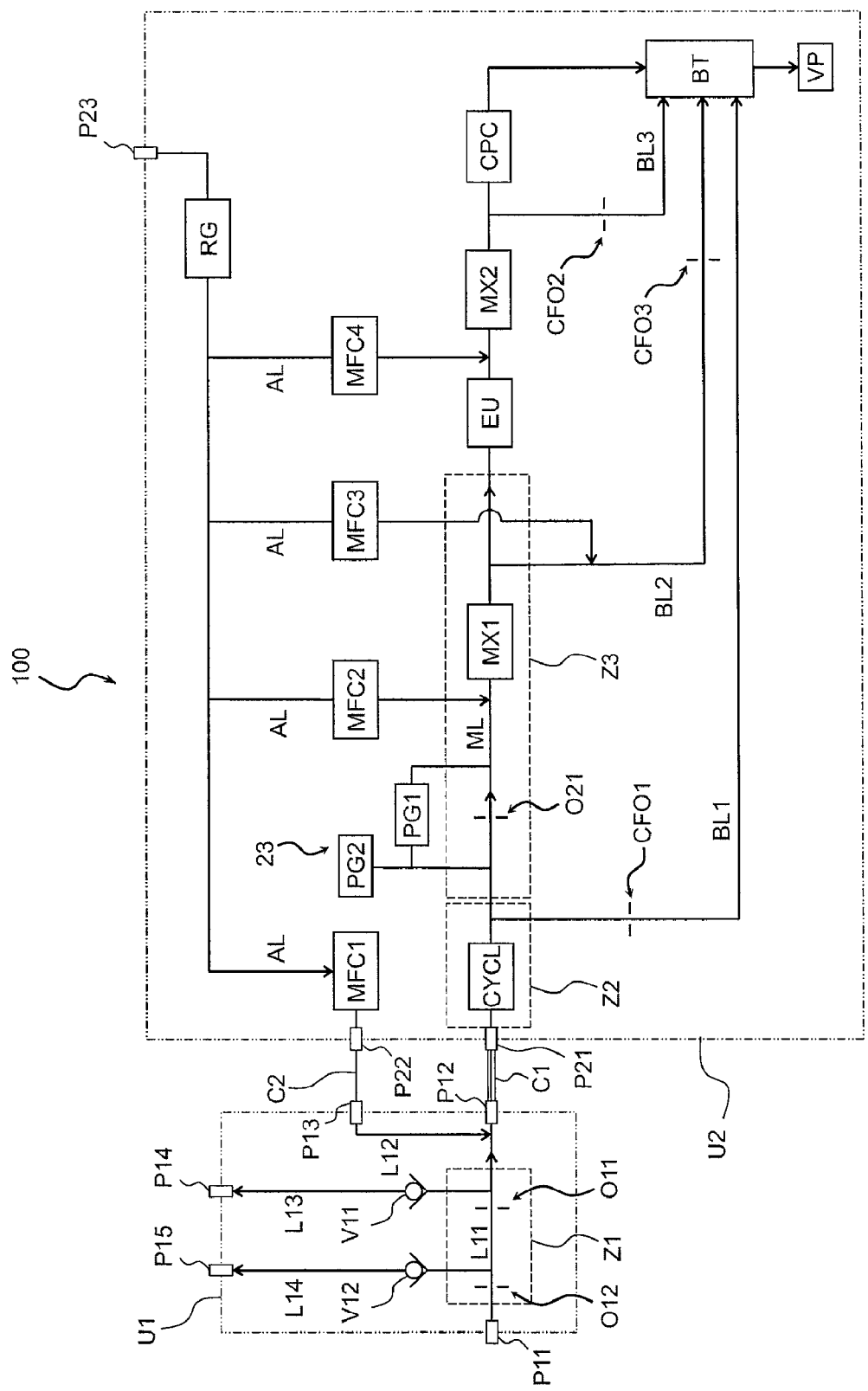
FIG. 3 is a general fluid circuit diagram of the particulate matter measurement device in accordance with this embodiment.

The body 2 is in a shape of, for example, a block, and an exhaust gas flow channel (L11) into which the exhaust gas from the exhaust gas pipe 1 is introduced penetrates inside of the body 2. In addition, a circumference of the body 2 is covered with a heat insulation material, not shown in the drawings, and a temperature of the body 2 is adjusted so that a predetermined area of the body 2 is not to be lower than or equal to a certain temperature by means of a mechanical temperature adjustor such as a thermostat. (Z1) in FIG. 3 shows the above-mentioned predetermined area where the temperature is adjusted.

Figure 2:
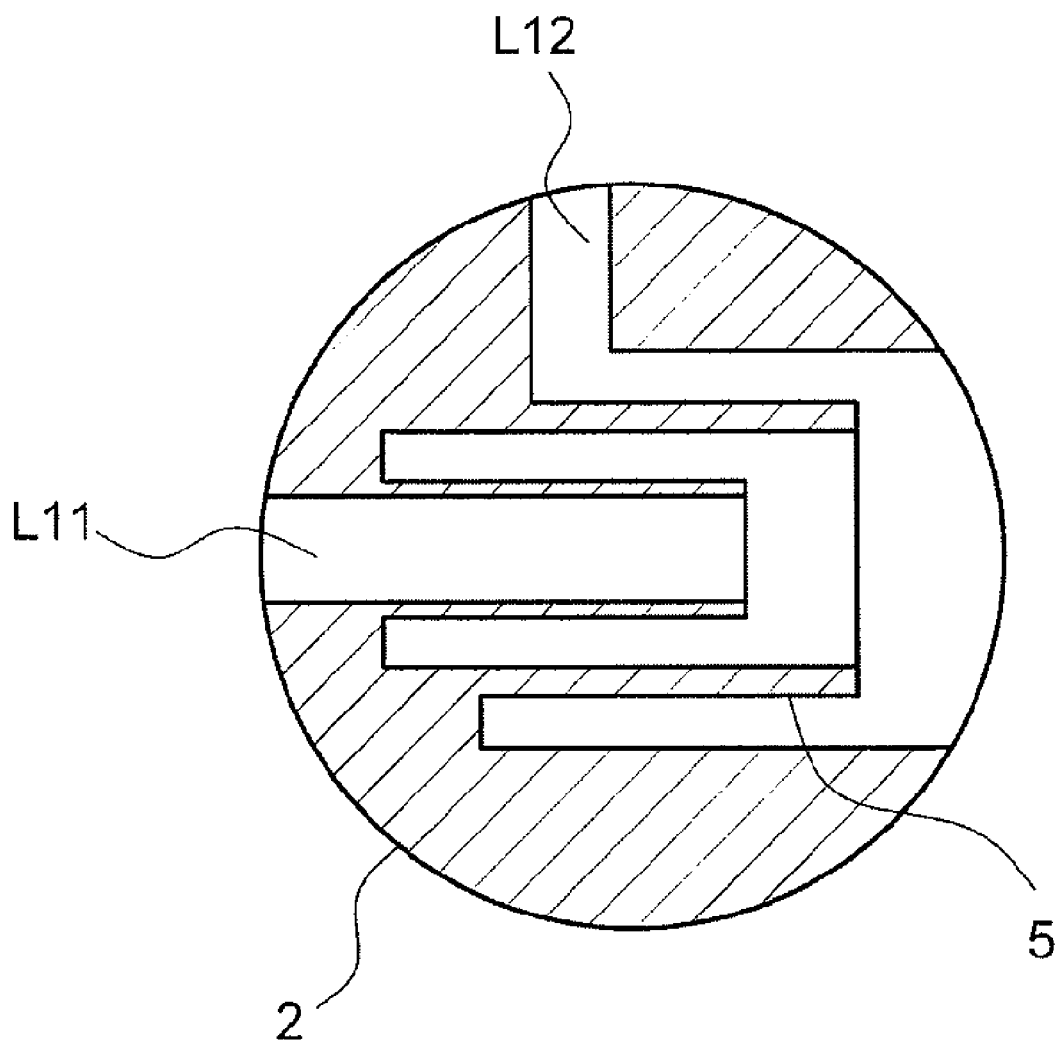
FIG. 2 is a cross-sectional view showing a first unit in accordance with this embodiment.

Next, the exhaust gas flow channel (L11) will be described in detail with reference to FIG. 3. A starting end of the exhaust gas flow channel (L11) opens as an exhaust gas introduction port (P11) on a surface, facing the exhaust gas pipe 1, of the body 2. Apart of the exhaust gas flowing in the exhaust gas pipe 1 is introduced, without being diluted, into the exhaust gas introduction port (P11) through a sampling pipe (C3). The sampling pipe (C3) is, as shown in FIG. 2, a straight pipe made of metal such as stainless or aluminum. One end of the sampling pipe (C3) is inserted into the exhaust gas pipe 1 from a side surface of the exhaust gas pipe 1 and the other end of the sampling pipe (C3) is connected to the exhaust gas introducing port (P11) and its mid-course is exposed to outside. Neither a heater nor a temperature adjusting mechanism is not attached to the sampling pipe (C3), and the sampling pipe (C3) comprises a metal pipe alone.

Figure 4:
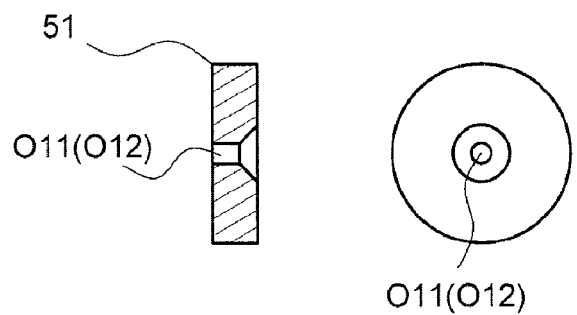
FIG. 4 is a detailed cross-sectional view of an orifice part in this embodiment.
Figure 5:
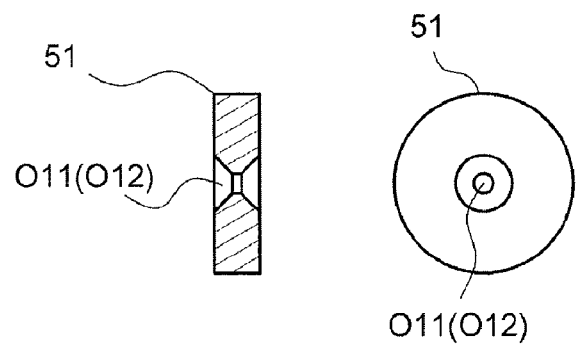
FIG. 5 is a detailed cross-sectional view of an orifice part in accordance with another embodiment.
Figure 6:
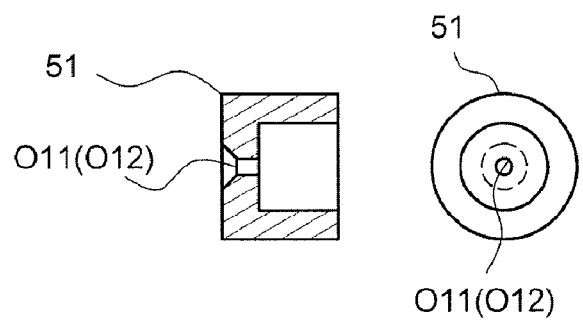
FIG. 6 is a detailed cross-sectional view of an orifice part in accordance with further different embodiment.

Two orifice parts (O11, O12), whose internal diameter is partially narrowed down, are arranged in serial at positions in the midstream of the exhaust gas flow channel (L11). Each of the orifice parts (O11), (O12) is, for example, as shown in FIG. 4, a through bore arranged to penetrate a disk-shaped orifice forming member 51 in its thickness direction. A downstream side or an upstream side of the through bore is formed into a spreading dished shape. A shape of the orifice forming member 51 may be, as shown in FIG. 5, a disk shape with spreading toward the downstream side and the upstream side of the through bore, or may be a simple through bore having the same diameter, although not shown in drawings. Furthermore, the orifice forming member 51 is not limited to the disk shape, and may be, for example as shown in FIG. 6, a cylindrical member whose one end opens. In FIG. 6, the orifice parts (O11), (O12) are arranged on a bottom plate of the cylindrical member.

Escape flow channels (L13, L14) are bifurcated from a downstream side of each orifice part (O11, O12), and pressure rising check valves (V11, V12) (for example, check valves) are arranged to prevent a pressure rise by letting a part of the exhaust gas escape to the escape flow channels (L13, L14) with mechanically opened by the pressure at a time when the pressure in the exhaust gas flow channel (L11) becomes equal to or bigger than a certain pressure.

A dilution gas flow channel (L12) where the dilution gas (for example, air) flows is connected to a position at a further downstream side of the orifice parts (O11, O12) locating at a downstream in the exhaust gas flow channel (L11). A starting end of the dilution gas flow channel (L12) opens as a dilution gas introduction port (P13) on a surface of the body 2 and the exhaust gas in the exhaust gas flow channel (L11) is diluted by the dilution gas introduced from the dilution gas introduction port (P13). The diluted exhaust gas (hereinafter called as the diluted exhaust gas) is derived from a terminal end, which opens on a surface of the body 2 as the exhaust gas deriving port (P12), of the exhaust gas flow channel (L11).

As shown in FIG. 2, a portion, connecting with the dilution gas flow channel (L12), of the exhaust gas flow channel (L11) is of a double-channel. Due to the double-channel structure, the dilution gas discharged from the dilution gas flow channel (L12) first touches an exterior pipe 5 of the exhaust gas flow channel (L11), and flows in an axial direction that is the same as a direction of the flow of the exhaust gas along a side surface of the exterior pipe 5, and then is mixed with the exhaust gas. On a condition that the exhaust gas flow channel (L11) is not of a double-channel and, for example, a discharge port of the dilution gas flow channel (L12) is directly arranged on the side surface of the exhaust gas flow channel (L11), a gas flow other than the axial direction such as to touch a surface facing the discharge port is generated in the exhaust gas flow channel (L11) due to an inflow of the dilution gas, which might lead to attachment of particulate matters to the surface facing the discharge port. In this case, the particulate matters fail to be carried efficiently to the second unit (U2).

The bracket mechanism 3 is, as shown in FIG. 1, made of a metal comprising a support base 31 that supports the body 2, and a clip part 32 that extends from the support base 31 and that is mounted on the exhaust gas pipe 1. The clip part 32 is in an annular plate shape and mounted on the exhaust gas pipe 1 in a state of pinching the exhaust gas pipe 1 from a radial direction, and connected to the support base 31 in a state of being able to change an angle to the support base 31 so as to set the support base 31 in an appropriate posture irrespective of an angle of the exhaust gas pipe 1. The sampling pipe (C3) penetrates the clip part 31 by elongating from the exhaust gas introduction port (P11) and is inserted into a side circumferential surface of the exhaust gas pipe 1 generally at right angle.

Next, the second unit (U2) will be explained briefly.

The second unit (U2) is so arranged, as shown in FIG. 1, each equipment and piping are housed in a casing 6.

The second unit (U2) is so arranged, as shown in FIG. 3, an exhaust gas inflowing port (P21) that is connected through the connecting pipe (C1) is arranged for the exhaust gas deriving port (P12) of the first unit (U1). Inside of the connecting pipe (C1) is kept at a certain temperature (about 47° C.) by the use of a pipe made of the electrically conductive Teflon (registered trademark).

As shown in FIG. 3, a main flow channel (ML) arranged inside of the casing 6 is connected to the exhaust gas inflowing port (P21), and a dust remover (CYCL) of a cyclone type, a flow rate measuring mechanism 23, a first dilution mixing unit (MX1), an evaporation unit (EU), a second dilution mixing unit (MX2) and a particulate matter measurement mechanism (CPC) (the condensation particle counter described in the background art) to count particulate matters are arranged in this order from an upstream side of the main flow channel (ML). In addition, a buffer tank (BT) and a suction pump (VP) are arranged in a further downstream side of the main flow channel (ML).

As mentioned, the diluted exhaust gas introduced from the exhaust gas inflowing port (P21) is introduced into the particulate matter measurement mechanism (CPC) through the main flow channel (ML), and then the particulate matters are counted. Each code (O21), (PG1), (PG2) is an orifice, a differential meter and an absolute pressure meter constituting the flow rate measuring mechanism 23.

In addition, bypass flow channels (BL1), (BL2), (BL3) each of which is connected to the buffer tank (BT) are bifurcated at predetermined portions of the main flow channel (ML). Critical orifices (CFO1), (CFO2), (CFO3) as being a constant flow rate mechanism are arranged on each bypass flow channel (BL1), (BL2), (BL3) so as to flow a gas of a constant flow rate.

Meanwhile, a code (P23) in FIG. 3 is a dilution gas supply port arranged in the casing 6, and a code (AL) in FIG. 3 is a plurality of internal dilution gas flow channels arranged in parallel and connected to the dilution gas supply port (P23) through a regulator (RG). Then it is so arranged that the dilution gas is supplied from the internal dilution gas flow channel (AL) to a given portion in the main flow channel (ML). Mass flow controllers (MFC1), (MFC2), (MFC3) and (MFC4) are arranged in the internal dilution gas flow channel (AL) so that the flow rate of the dilution gas flowing in the internal dilution gas flow channel (AL) can be controlled. In addition, one internal dilution gas flow channel (AL) among the internal dilution gas flow channels (AL) is connected from the dilution gas deriving port (P22) arranged in the casing 6 to the dilution gas introduction port (P13) of the first unit (U1) through the second connecting pipe (C2).

A code (Z2) and a code (Z3) show an area where the temperature is kept at a constant value, the area (Z2) is kept at, for example, 47° C., and the area (Z3) is kept at, for example, 191° C.

Next, an operation of the particulate matter measurement device 100 having the above-mentioned arrangement will be explained.

The exhaust gas is introduced from the exhaust gas pipe 1 into the first unit (U1) with its flow rate restricted by two orifice parts (O11), (O12). An internal diameter of the orifice (O11), (O12) is set based on the estimated maximum pressure in the exhaust gas pipe 1 and the maximum flow rate that can be accepted by the second unit (U2), however, on the condition that the pressure in the exhaust gas pipe 1 exceeds the estimated maximum pressure and a flow rate exceeding the maximum flow rate is introduced into the second unit (U2), the pressure rising check valves V11, V12 are automatically opened by the pressure rise at this time, and a part of the exhaust gas is let out from escape ports (P14), (P15) so that the exhaust gas of not exceeding the maximum flow rate is sampled.

Then the exhaust gas is diluted by the dilution gas supplied from the dilution gas flow channel (L12). Since the dilution gas is introduced at a room temperature, the exhaust gas is diluted and its temperature is lowered as well.

As mentioned, the diluted exhaust gas diluted by the first unit (U1) is introduced into the second unit (U2). In the second unit (U2), a certain flow rate of the diluted exhaust gas is discarded through a bypass flow rate (BL1) by an action of the critical orifice (CFO1).

A dilution ratio is controlled by a mass flow controller (MFC1) arranged in the flow channel (AL) of the dilution gas.

Namely, in case that a flow rate of the introduced sampled exhaust gas is set (qs), a flow rate of the dilution gas controlled by the mass flow controller (MFC1) is set (Qa), a flow rate of the diluted exhaust gas discarded through the critical orifice (CFO1) after dilution is set (Qb), and a flow rate of the remaining diluted exhaust gas flowing in the main flow channel (ML) is set (Qm), the following equation is satisfied.

$$qs=Qb+Qm-Qa$$

Since (Qb) is a given constant value, Qm is a given value because it is measured by a flow meter arranged in the main flow channel (ML), and (Qa) is an amount controlled by the mass flow controller (MFC1), it is possible to calculate (qs) indirectly based on these (Qa), (Qb) and (Qm).

In addition, the dilution ratio (rd) in the first unit (U1) can be obtained from the following equation, and this equation proves that the dilution ratio can be controlled by the mass flow controller (MFC1).

$$rd=qs/(qs+Qa)=(Qb+Qm-Qa)/(Qb+Qm)$$

Later, the diluted exhaust gas is diluted by two steps of dilution mixing units (MX1), (MX2). While the diluted exhaust gas is diluted, the diluted exhaust gas is evaporated by an evaporation unit (EU) based on the specification. Similar to the dilution by the first unit (U1), since the flow rate of the dilution gas is controlled by the mass flow controllers (MFC2), (MFC4) and a predetermined flow rate is discarded by the critical orifices (CFO2), (CFO3), and a mass flow controller (MFC3), it is possible to calculate the dilution ratio uniquely.

Since a number of the particulate matters contained in the diluted exhaust gas is counted by the particulate matter measurement mechanism (CPC) and the dilution ratio is calculated as mentioned, it is possible to calculate the number of the particulate matters contained in a unit flow rate of the exhaust gas, namely a concentration based on the dilution ratio and the counted number by the particulate matter measurement mechanism (CPC).

In accordance with this embodiment having the above-mentioned arrangement, since the particulate matter measurement device 100 is divided into the first unit (U1) and the second unit (U2) and the first unit (U1) is directly mounted on the exhaust gas pipe 1 and arranged near the exhaust gas pipe 1, it is possible to make a length of the sampling pipe (C3) that samples the exhaust gas pipe 1 and introduces the sampled gas into the first unit (U1) extremely short, which contributes to avoiding drop of the temperature in the sampling pipe (C3). As a result, even though a metal pipe alone is used for the sampling pipe (C3) without using a hot hose, it is possible to avoid a problem such that particle matters attach inside of the sampling pipe (C3). Accordingly, it is possible to reduce a cost and to improve resistance to heat largely since the sampling pipe (C3) comprises the metal pipe alone.

In addition, for the first unit (U1), since the heat from the exhaust gas pipe 1 is transferred to the body 2 through the sampling pipe (C3) or the bracket 3, a heater with a small capacity at low cost will do as a heater arranged for the body 2.

Furthermore, since no problem concerning temperature will be generated because the exhaust gas is diluted by the first unit (U1) and the temperature of the exhaust gas after diluted is lowered, there is no need of keeping the connecting pipe (C2) between the first unit (U1) and the second unit (U2) at a high temperature. Also due to this arrangement, it is possible to reduce a cost and to simplify the arrangement.

In addition, since the orifice parts (O11), (O12) are arranged for the first unit (U1) and the pressure rising check valves (V11), (V12) are arranged on the downstream of the orifice parts (O11), (O12), in spite of a case that the pressure in the exhaust gas pipe 1 is approximate to the atmospheric pressure by the setting of the orifice valves (O11), (O12), the pressure in a side of the particulate matters measurement device 100 will not be at a negative pressure. Furthermore, even though the pressure in the exhaust gas pipe 1 becomes high by the setting of the orifice valves (O11), (O12), it is possible to keep the pressure in the side of the particulate matters measurement device 100 at a pressure smaller than or equal to the set value so as to increase the resistance to pressure, thereby expanding a measurable range of the pressure.

In addition, since the second unit (U2) also can conduct dilution, it is possible to set the dilution ratio at a big value in addition to the dilution by the first unit (U1). Furthermore, since the number of the particle can be measured by the second unit (U2) by itself, it is possible to use the second unit (U2) alone with omitting the first unit (U1) for a usage that requires neither a big dilution ratio nor the resistance to pressure.

The present claimed invention is not limited to the above-mentioned embodiment.

For example, a number of the orifice part of the first unit may be one, or more than three. The bracket may not have the arrangement in the above-mentioned embodiment, and furthermore is not necessarily required. For example, the body of the first unit may be placed near the exhaust gas pipe and may be connected only by the sampling pipe.

In addition, the dilution gas may be supplied to the first unit independently from the second unit.

It is a matter of course that the present claimed invention is not limited to the above-mentioned embodiment and may be variously modified without departing from a spirit of the invention.

Explanation of Code

100 . . . particulate matter measurement device
1 . . . exhaust gas pipe
2 . . . body
U1 . . . first unit
U2 . . . second unit
C1 . . . connecting pipe
L11 . . . exhaust gas flow channel
O11 . . . orifice part
O12 . . . second orifice part
V11 . . . pressure rising check valve
V12 . . . second pressure rising check valve
L12 . . . dilution gas flow channel
CPC . . . particulate matter measurement mechanism

The invention claimed is:

1. A particulate matter measurement device that is to measure a particulate matter contained in an exhaust gas emitted from an internal combustion engine and that comprises a first unit arranged near an exhaust gas pipe of the internal combustion engine, a second unit arranged separately from the first unit and a connecting pipe arranged between the first unit and the second unit, wherein the first unit comprises
a body that has an exhaust gas flow channel from one end of which the exhaust gas is introduced, an orifice part arranged in the exhaust gas flow channel, a pressure rising check valve that is connected to the exhaust gas flow channel and that prevents a rise of the pressure by letting a part of the exhaust gas escape by mechanically opening by the pressure at a time when the pressure in the exhaust gas flow channel becomes bigger than or equal to a certain amount, and a dilution gas flow channel that is connected to a downstream side of the orifice part in the exhaust gas flow channel and that introduces the dilution gas into the exhaust gas flow channel, and that is so arranged to derive the diluted exhaust gas as being the exhaust gas diluted by the dilution gas from the other end of the exhaust gas flow channel, the second unit comprises a particulate matter measurement mechanism that introduces the diluted exhaust gas derived from the first unit through the connecting pipe and that measures the particulate matter contained in the introduced diluted exhaust gas.

2. The particulate matter measurement device described in claim 1, wherein the pressure rising check valve is arranged on the downstream side of the orifice part, a second orifice part is arranged on the upstream side of the orifice part, and a second pressure rising check valve is arranged between the orifice part and the second orifice part in the exhaust gas flow channel.

3. The particulate matter measurement device described in claim 1, wherein the first unit further comprises a bracket mechanism for mounting the body on the exhaust gas pipe.

* * * * *